(12) United States Patent
Musa et al.

(10) Patent No.: US 11,319,301 B2
(45) Date of Patent: May 3, 2022

(54) HALOGEN COMPLEXES OF COMPOUNDS COMPRISING AT LEAST ONE ETHER, THIOETHER, AND/OR IMINE MOIETY AND AT LEAST TWO LACTAM MOIETIES

(71) Applicant: ISP INVESTMENTS LLC, Wilmington, DE (US)

(72) Inventors: Osama M. Musa, Bedminster, NJ (US); Melissa J. Goodwin, Helgelo (NL); Benjamin W. Steed, Durham (GB); Jonathan W. Steed, Durham (GB)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 16/634,683

(22) PCT Filed: Jul. 26, 2018

(86) PCT No.: PCT/US2018/043898
§ 371 (c)(1),
(2) Date: Jan. 28, 2020

(87) PCT Pub. No.: WO2019/023453
PCT Pub. Date: Jan. 31, 2019

(65) Prior Publication Data
US 2020/0231574 A1 Jul. 23, 2020

Related U.S. Application Data

(60) Provisional application No. 62/538,540, filed on Jul. 28, 2017.

(51) Int. Cl.
*C07D 403/12* (2006.01)
*C07D 401/12* (2006.01)

(52) U.S. Cl.
CPC .......... *C07D 403/12* (2013.01); *C07D 401/12* (2013.01)

(58) Field of Classification Search
CPC ........................... C07D 403/12; C07D 401/12
See application file for complete search history.

(56) References Cited

U.S. PATENT DOCUMENTS

| | | | | |
|---|---|---|---|---|
| 4,842,858 A | * | 6/1989 | Tracy | A01N 59/12 424/78.18 |
| 4,886,890 A | * | 12/1989 | Chaudhuri | C07D 207/263 548/519 |
| 5,672,765 A | * | 9/1997 | Marhold | C07B 39/00 564/152 |
| 9,351,484 B2 | * | 5/2016 | Musa | B01D 53/1468 |
| 9,993,559 B2 | * | 6/2018 | Musa | A61Q 19/00 |
| 2012/0148514 A1 | * | 6/2012 | Musa | C09D 7/20 424/60 |
| 2014/0045698 A1 | * | 2/2014 | Musa | A01N 43/653 504/358 |
| 2016/0271254 A1 | | 9/2016 | Musa et al. | |
| 2020/0188408 A1 | * | 6/2020 | Musa | A61K 31/44 |

FOREIGN PATENT DOCUMENTS

| | | | | |
|---|---|---|---|---|
| DE | 2611602 A1 | * | 9/1977 | ......... C07D 207/267 |
| WO | WO8800184 A1 | | 1/1988 | |

OTHER PUBLICATIONS

Wassermann; Naunyn-Schmiedeberg's Archives of Pharmacology 1972, 275, 251-261 (Year: 1972).*
Schenck; J Pharm Sci, 1979, 68, 1505. (Year: 1979).*
IUPAC. Compendium of Chemical Terminology, 2nd ed. (the "Gold Book"). Compiled by A. D. McNaught and A. Wilkinson. Blackwell Scientific Publications, Oxford (1997): Entry for "Imines", 1 page, https://doi.org/10.1351/goldbook.I02696 (Year: 1997).*
Botero Cid; J. Med. Chem. 2000, 43, 11, 2155-2164. (Year: 2000).*
Perrin; Dalton Trans., 2016, 45, 12181-12187. (Year: 2016).*
Goodwin; Cryst. Growth Des. 2017, 17, 5552-5558, with supporting information, 12 pages. (Year: 2017).*
Bigliardi; International Journal of Surgery 2017, 44, 260-268. (Year: 2017).*
Goodwin; Cryst. Growth Des. 2018, 18, 701-709. (Year: 2018).*
Schenck; Makromolekulare Chemie 1980, 181, 1871-1888. https://doi.org/10.1002/macp.1980.021810909 (Year: 1980).*
Referenced cited in the international search report of PCT Application No. PCT/US2018/043898 published on Jan. 31, 2019 under publication No. WO2019/023453 A1.

* cited by examiner

*Primary Examiner* — Daniel R Carcanague
(74) *Attorney, Agent, or Firm* — William J. Davis; Nathalie Tietcheu

(57) ABSTRACT

The disclosed and/or claimed inventive concept(s) provides a complex of at least one halogen and a compound comprising at least one ether, thioether, and/or imine moiety and at least two lactam moieties. The disclosed and/or claimed inventive concept(s) further provides compositions comprising the complexes and applications thereof in various industrial areas including personal care, home care, pharmaceuticals, antimicrobials, disinfectants, biocides, germicides, and coatings.

8 Claims, No Drawings

HALOGEN COMPLEXES OF COMPOUNDS COMPRISING AT LEAST ONE ETHER, THIOETHER, AND/OR IMINE MOIETY AND AT LEAST TWO LACTAM MOIETIES

BACKGROUND

Field of the Invention

The disclosed and/or claimed inventive concept(s) provides complexes of halogen(s) and compounds comprising at least one ether, thioether, and/or imine moieties and at least two lactam moieties. The disclosed and/or inventive concept(s) further provides compositions comprising the complexes and applications thereof in various industrial areas including home and personal care, coatings and pharmaceuticals.

Description of Related Art

Complexes of povidone (polyvinyl pyrrolidone) and iodine have remained popular for decades in wound healing applications due to their safety and efficacy. The factors that have been cited as crucial for widespread applications of povidone-iodine complexes include their ability to penetrate biofilms, lack of associated resistance, anti-inflammatory properties, low cytotoxicity and good tolerability.

A review of current concepts and practices of povidone iodine in wound healing is provided by Bigliardi and co-workers in International Journal of Surgery, 2017, Volume 44, 260-268.

A description of halogen and hydrogen bonding in povidone iodine and related co-phases is provided by Goodwin and co-workers in Crystal Growth and Design, 2017, Volume 10, 5552-5558.

One of the earliest attempts to describe the structure of povidone-iodine complexes was authored by Schenck and co-workers in Journal of Pharmaceutical Sciences, 1979, Volume 68, 1505-1509.

The coordination chemistry of a bis(pyrrolidone) ether ligand was explored in detail by Perrin and co-workers in Dalton Transactions, 2014, Volume 43, 3153-3161.

U.S. Pat. No. 6,228,354 discloses a water-resistant film-forming antimicrobial skin-preparation comprising a polyvinyl lactam, a broad spectrum antimicrobial agent, a copolymer of polyacrylate/polyoctylacrylamide, a pH sensitive acrylic polymer, and an alcohol.

U.S. Pat. No. 4,842,858 discloses a stable iodine complex formed from the association of iodine with a pyrrolidonyl surfactant and its use in therapeutic, environmental and industrial applications.

U.S. Pat. No. 9,993,559 discloses a class of symmetrical and asymmetrical N-alkyl lactam ethers and uses of these ethers are in performance chemicals, personal care, and pharmaceutical fields.

It has been found that compositions according to the disclosed and/or claimed inventive concept(s) have unique and important performance attributes due to which they can be advantageously used in various industrial applications including, but not limited to home and personal care, coatings and pharmaceuticals.

SUMMARY

In a first aspect, the disclosed and/or claimed inventive concept(s) provides a complex of at least one halogen and a compound comprising at least one ether, thioether, and/or imine moiety and at least two lactam moieties.

In a second aspect, the disclosed and/or claimed inventive concept(s) provides a composition comprising a complex of at least one halogen and a compound comprising at least one ether, thioether, and/or imine moiety and at least two lactam moieties. Non-limiting examples of the compositions include personal care compositions, home care compositions, household, industrial and institutional compositions, pharmaceutical compositions, preservative compositions, disinfectant compositions, biocidal compositions, germicidal compositions, antimicrobial compositions, coating compositions, construction compositions, oilfield compositions, drilling fluids, drilling muds, cementing fluids, servicing fluids, gravel packing muds, fracturing fluids, completion fluids, workover fluids, spacer fluids, food compositions, adhesives, inks, papers, polishes, membranes, metal working fluids, plastics, textiles, printing compositions, lubricants, agrochemicals, and wood-care compositions. In one non-limiting embodiment, the composition is a personal care composition, home care composition, pharmaceutical composition, disinfectant composition, biocidal composition, germicidal composition, antimicrobial composition, or coating composition.

In a third aspect, the disclosed and/or claimed inventive concept(s) provides a personal care, home care, pharmaceutical, antimicrobial, disinfectant, biocidal, germicidal, or coating composition comprising a complex of at least one halogen and a compound comprising at least one ether, thioether, and/or imine moiety and at least two lactam moieties.

DETAILED DESCRIPTION

Before explaining at least one aspect of the disclosed and/or claimed inventive concept(s) in detail, it is to be understood that the disclosed and/or claimed inventive concept(s) is not limited in its application to the details of construction and the arrangement of the components or steps or methodologies set forth in the following description. The disclosed and/or claimed inventive concept(s) is capable of other aspects or of being practiced or carried out in various ways. Also, it is to be understood that the phraseology and terminology employed herein is for the purpose of description and should not be regarded as limiting.

Unless otherwise defined herein, technical terms used in connection with the disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications referenced in any portion of this application are herein expressly incorporated by reference herein their entirety to the same extent as if each individual patent or publication was specifically and individually indicated to be incorporated by reference.

All of the articles and/or methods disclosed herein can be made and executed without undue experimentation in light of the present disclosure. While the articles and methods of the disclosed and/or claimed inventive concept(s) have been described in terms of aspects, it will be apparent to those of ordinary skill in the art that variations may be applied to the articles and/or methods and in the steps or in the sequence of steps of the method described herein without departing from the concept, spirit and scope of the disclosed and/or claimed inventive concept(s). All such similar substitutes and modifications apparent to those skilled in the art are deemed to be within the spirit, scope and concept of the disclosed and/or claimed inventive concept(s).

As utilized in accordance with the disclosure, the following terms, unless otherwise indicated, shall be understood to have the following meanings.

The use of the word "a" or "an" when used in conjunction with the term "comprising" may mean "one," but it is also consistent with the meaning of "one or more," "at least one," and "one or more than one." The use of the term "or" is used to mean "and/or" unless explicitly indicated to refer to alternatives only if the alternatives are mutually exclusive, although the disclosure supports a definition that refers to only alternatives and "and/or".

Throughout this application, the term "about" is used to indicate that a value includes the inherent variation of error for the quantifying device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent.

The use of the term "at least one" will be understood to include one as well as any quantity more than one, including but not limited to, 1, 2, 3, 4, 5, 10, 15, 20, 30, 40, 50, 100, etc. The term "at least one" may extend up to 100 or 1000 or more depending on the term to which it is attached. In addition, the quantities of 100/1000 are not to be considered limiting as lower or higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first", "second", "third", "fourth", etc.) is solely for the purpose of differentiating between two or more items and, unless otherwise stated, is not meant to imply any sequence or order or importance to one item over another or any order of addition.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "or combinations thereof" as used herein refers to all permutations and combinations of the listed items preceding the term. For example, "A, $BX_n$, $BX_{n+1}$, or combinations thereof" is intended to include at least one of: A, $BX_n$, $BX_{n+1}$, $ABX_n$, $ABX_{n+1}$, $BX_nBX_{n+1}$, or $ABX_nBX_{n+1}$ and, if order is important in a particular context, also $BX_nA$, $BX_{n+1}A$, $BX_{n+1}BX_n$, $BX_{n+1}BX_nA$, $BX_nBX_{n+1}A$, $ABX_{n+1}BX_n$, $BX_nABX_{n+1}$, or $BX_{n+1}ABX_n$. Continuing with this example, expressly included are combinations that contain repeats of one or more item or term, such as $BX_nBX_n$, AAA, $MBX_n$, $BX_nBX_nBX_{n+1}$, $AAABX_nBX_{n+1}BX_{n+1}BX_{n+1}BX_{n+1}$, $BX_{n+1}BX_nBX_nAAA$, $BX_{n+1}A$, $BX_nABX_nBX_n$, and so forth. The skilled artisan will understand that typically there is no limit on the number of items or terms in any combination, unless otherwise apparent from the context.

The term "each independently selected from the group consisting of means when a group appears more than once in a structure, that group may be selected independently each time it appears.

The term "hydrocarbyl" includes straight-chain and branched-chain alkyl, alkenyl, alkynyl, cycloalkyl, cycloalkenyl, aryl groups, and combinations thereof with optional heteroatom(s). A hydrocarbyl group may be mono-, di- or polyvalent.

The term "alkyl" refers to a functionalized or unfunctionalized, monovalent, straight-chain, branched-chain, or cyclic $C_1$-$C_{60}$ hydrocarbyl group optionally having one or more heteroatoms. In one non-limiting embodiment, an alkyl is a $C_1$-$C_{45}$ hydrocarbyl group. In another non-limiting embodiment, an alkyl is a $C_1$-$C_{30}$ hydrocarbyl group. Non-limiting examples of alkyl include methyl, ethyl, n-propyl, isopropyl, n-butyl, isobutyl, tert-butyl, n-pentyl, isopentyl, n-hexyl, n-heptyl, n-octyl, 2-ethylhexyl, tert-octyl, iso-norbornyl, n-dodecyl, tert-dodecyl, n-tetradecyl, n-hexadecyl, n-octadecyl, n-eicosyl, cyclobutyl, cyclopentyl, cyclohexyl, and the like. The definition of "alkyl" also includes groups obtained by combinations of straight-chain, branched-chain and/or cyclic structures.

The term "aryl" refers to a functionalized or unfunctionalized, monovalent, aromatic hydrocarbyl group optionally having one or more heteroatoms. The definition of aryl includes carbocyclic and heterocyclic aromatic groups. Non-limiting examples of aryl groups include phenyl, naphthyl, indenyl, indanyl, azulenyl, fluorenyl, anthracenyl, furyl, thienyl, pyridyl, pyrrolyl, oxazolyl, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, carbazolyl, acridinyl, phenazinyl, phenothiazinyl, phenoxyazinyl, pyrazolo[1,5-c]triazinyl, and the like.

The term "aralkyl" refers to an alkyl group comprising one or more aryl substituent(s) wherein "aryl" and "alkyl" are as defined above. Non-limiting examples of aralkyl groups include benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like.

The term "alkylene" refers to a functionalized or unfunctionalized, divalent, straight-chain, branched-chain, or cyclic $C_1$-$C_{40}$ hydrocarbyl group optionally having one or more heteroatoms. In one non-limiting embodiment, an alkylene is a $C_1$-$C_{30}$ group. In another non-limiting embodiment, an alkylene is a $C_1$-$C_{20}$ group. Non-limiting examples of alkylene groups include:

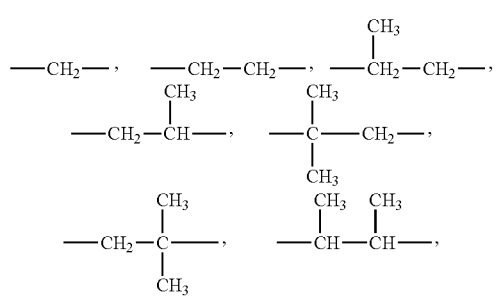

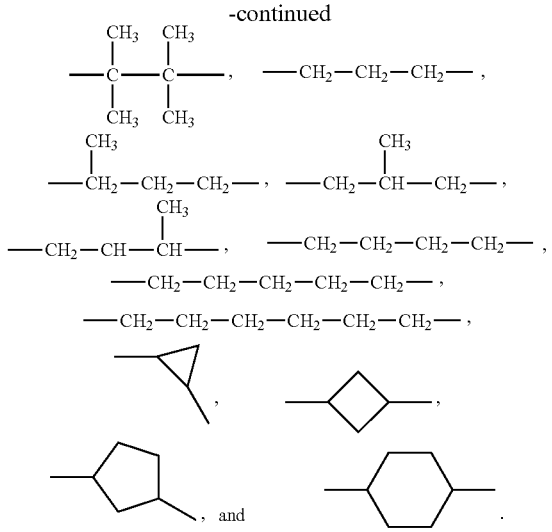

The term "arylene" refers to a functionalized or unfunctionalized, divalent, aromatic hydrocarbyl group optionally having one or more heteroatoms. The definition of arylene includes carbocyclic and heterocyclic groups. Non-limiting examples of arylene groups include phenylene, naphthylene, pyridinylene, and the like.

The term "heteroatom" refers to oxygen, nitrogen, sulfur, silicon, phosphorous, or halogen. The heteroatom(s) may be present as a part of one or more heteroatom-containing functional groups. Non-limiting examples of heteroatom-containing functional groups include ether, hydroxy, epoxy, carbonyl, carboxamide, carboxylic ester, carboxylic acid, imine, imide, amine, sulfonic, sulfonamide, phosphonic, and silane groups. The heteroatom(s) may also be present as a part of a ring such as in heteroaryl and heteroarylene groups.

The term "halogen" refers to chlorine, fluorine, bromine or iodine. This definition of halogen encompasses molecular forms of iodine, bromine, chlorine and fluorine as well as halogen-containing molecules such as iodides, bromides, chlorides and fluorides. A halogen may possess any of the known oxidation states of −1, 0, +1, +3, +5 and +7.

The term "ammonium" includes protonated $NH_3$ and protonated primary, secondary, and tertiary organic amines.

The term "functionalized" with reference to any moiety refers to the presence of one or more functional groups in the moiety. Various functional groups may be introduced in a moiety by way of one or more functionalization reactions known to a person having ordinary skill in the art. Non-limiting examples of functionalization reactions include: alkylation, epoxidation, sulfonation, hydrolysis, amidation, esterification, hydroxylation, dihydroxylation, amination, ammonolysis, acylation, nitration, oxidation, dehydration, elimination, hydration, dehydrogenation, hydrogenation, acetalization, halogenation, dehydrohalogenation, Michael addition, aldol condensation, Canizzaro reaction, Mannich reaction, Clasien condensation, Suzuki coupling, and the like. In one non-limiting embodiment, the term "functionalized" with reference to any moiety refers to the presence of one more functional groups selected from the group consisting of alkyl, alkenyl, hydroxyl, carboxyl, halogen, alkoxy, amino, imino, and combinations thereof, in the moiety.

The term "monomer" refers to a small molecule that chemically bonds during polymerization to one or more monomers of the same or different kind to form a polymer.

The term "polymer" refers to a large molecule comprising one or more types of monomer residues (repeating units) connected by covalent chemical bonds. By this definition, polymer encompasses compounds wherein the number of monomer units may range from very few, which more commonly may be called as oligomers, to very many.

Non-limiting examples of polymers include homopolymers, and non-homopolymers such as copolymers, terpolymers, tetrapolymers and the higher analogues. The polymer may have a random, block, and/or alternating architecture.

The term "homopolymer" refers to a polymer that consists essentially of a single monomer type.

The term "non-homopolymer" refers to a polymer that comprises more than one monomer types.

The term "copolymer" refers to a non-homopolymer that comprises two different monomer types.

The term "terpolymer" refers to a non-homopolymer that comprises three different monomer types.

The term "branched" refers to any non-linear molecular structure. The term includes both branched and hyper-branched structures.

The term "moiety" refers to a part or a functional group of a molecule.

The term "complex" refers to a molecular architecture wherein two or more chemical entities are held together by non-covalent chemical bonds.

The terms "personal care composition" and "cosmetics" refer to compositions intended for use on or in the human body, such as skin, sun, hair, oral, cosmetic, and preservative compositions, including those to alter the color and appearance of skin and hair.

The term "pharmaceutical composition" refers to any composition comprising at least one pharmaceutically active ingredient, as well as any product which results, directly or indirectly, from combination, complexation, or aggregation of any two or more of the ingredients, from dissociation of one or more of the ingredients, or from other types of reactions or interactions of one or more of the ingredients.

The term "coating composition" refers to an aqueous-based or solvent-based liquid composition that may be applied to a substrate and thereafter solidified (for example, by radiation, air curing, post-crosslinking or ambient temperature drying) to form a hardened coating on the substrate.

The term "antimicrobial composition" refers to any composition that is effective against pathogenic microorganisms, including but not limited to bacteria, fungi, viruses, protozoa, and biofilms. Antimicrobial compositions can be used to disperse, remove, inhibit, reduce, or prevent microbial growth.

All percentages, ratio, and proportions used herein are based on a weight basis unless other specified.

In a first aspect, the disclosed and/or claimed inventive concept(s) provides a complex of at least one halogen and a compound comprising at least one ether, thioether, and/or imine moiety and at least two lactam moieties.

In one non-limiting embodiment, the compound comprising at least one ether, thioether, and/or imine moiety and at least two lactam moieties has a structure:

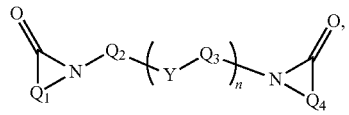

wherein each Y is independently selected from the group consisting of —O—, —S—, —NR—, and combinations thereof; each R is independently selected from the group consisting of hydrogen, alkyl,

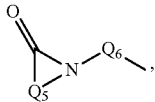

and combinations thereof; each $Q_1$, $Q_2$, $Q_3$, $Q_4$, $Q_5$ and $Q_6$ is independently a functionalized or unfunctionalized alkylene; and n has a value$\geq 1$.

In one non-limiting embodiment, each $Q_1$, $Q_2$, $Q_3$, $Q_4$, $Q_5$ and $Q_6$ is independently selected from the group consisting of functionalized and unfunctionalized $C_1$-$C_{12}$ alkylene. Non-limiting examples of such alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, and —$CH_2$—$CH_2$—$CH_2$—$CH_2$—$CH_2$—$CH_2$—.

In another non-limiting embodiment, each $Q_1$, $Q_2$, $Q_3$, $Q_4$, $Q_5$ and $Q_6$ is independently selected from the group consisting of functionalized and unfunctionalized $C_2$-$C_6$ alkylene. Non-limiting examples of such alkylene groups include:

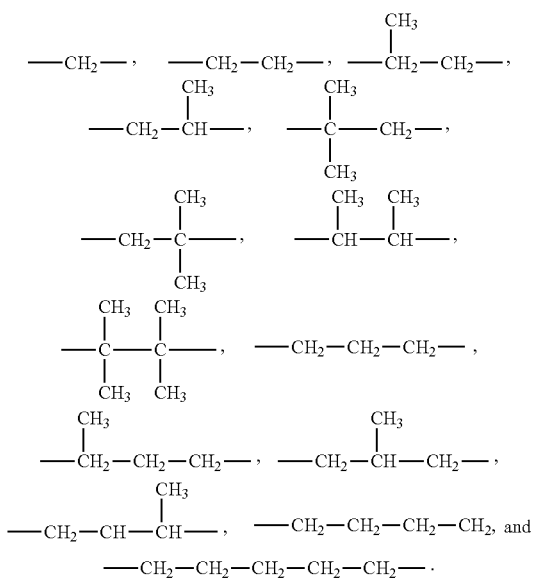

In one non-limiting embodiment, each R is independently selected from the group consisting of hydrogen, methyl and combinations thereof.

In one non-limiting embodiment, the compound comprising at least one ether, thioether, and/or imine moiety and at least two lactam moieties has a structure:

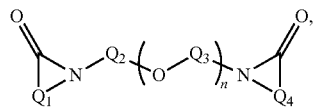

wherein each $Q_1$, $Q_2$, $Q_3$, and $Q_4$ is independently a functionalized or unfunctionalized alkylene and n has a value$\geq 1$.

In one non-limiting embodiment, each $Q_1$, $Q_2$, $Q_3$, and $Q_4$ is independently selected from the group consisting of functionalized and unfunctionalized $C_1$-$C_{12}$ alkylene. Non-limiting examples of such alkylene groups include —$CH_2$—, —$CH_2$—$CH_2$—, —$CH(CH_3)$—$CH_2$—, —$CH_2$—$CH(CH_3)$—, —$C(CH_3)_2$—$CH_2$—, —$CH_2$—$C(CH_3)_2$—, —$CH(CH_3)$—$CH(CH_3)$—, —$C(CH_3)_2$—$C(CH_3)_2$—, —$CH_2$—$CH_2$—$CH_2$—, —$CH(CH_3)$—$CH_2$—$CH_2$—, —$CH_2$—$CH(CH_3)$—$CH_2$—, —$CH_2$—$CH_2$—$CH(CH_3)$—, —$CH_2$—$CH_2$—$CH_2$—$CH_2$—, —$CH_2$—$CH_2$—$CH_2$—$CH_2$—$CH_2$—, and —$CH_2$—$CH_2$—$CH_2$—$CH_2$—$CH_2$—$CH_2$—.

In one non-limiting embodiment, each $Q_1$, $Q_2$, $Q_3$, and $Q_4$ is independently selected from the group consisting of functionalized and unfunctionalized $C_2$-$C_6$ alkylene. Non-limiting examples of such alkylene groups include:

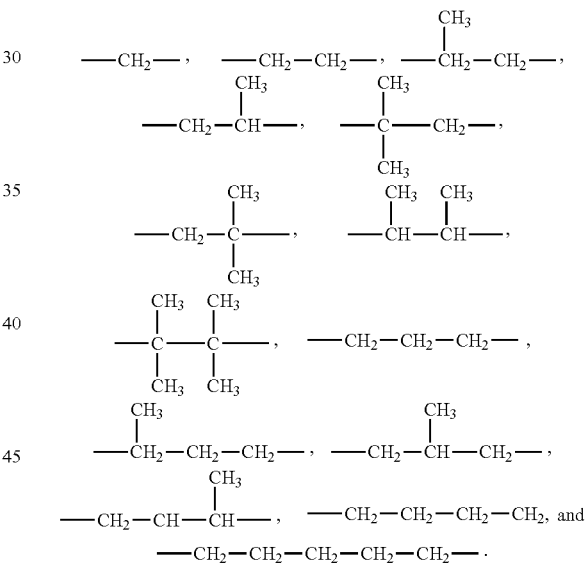

In one non-limiting embodiment, n has a value ranging from 1 to about 1000. In another non-limiting embodiment, n has a value ranging from 1 to about 100. In yet another non-limiting embodiment, n has a value ranging from 1 to about 10.

In one non-limiting embodiment, the compound comprising at least one ether, thioether, and/or imine moiety and at least two lactam moieties has a structure selected from the group consisting of:

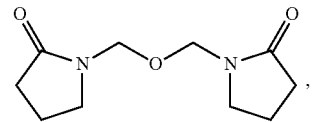

-continued

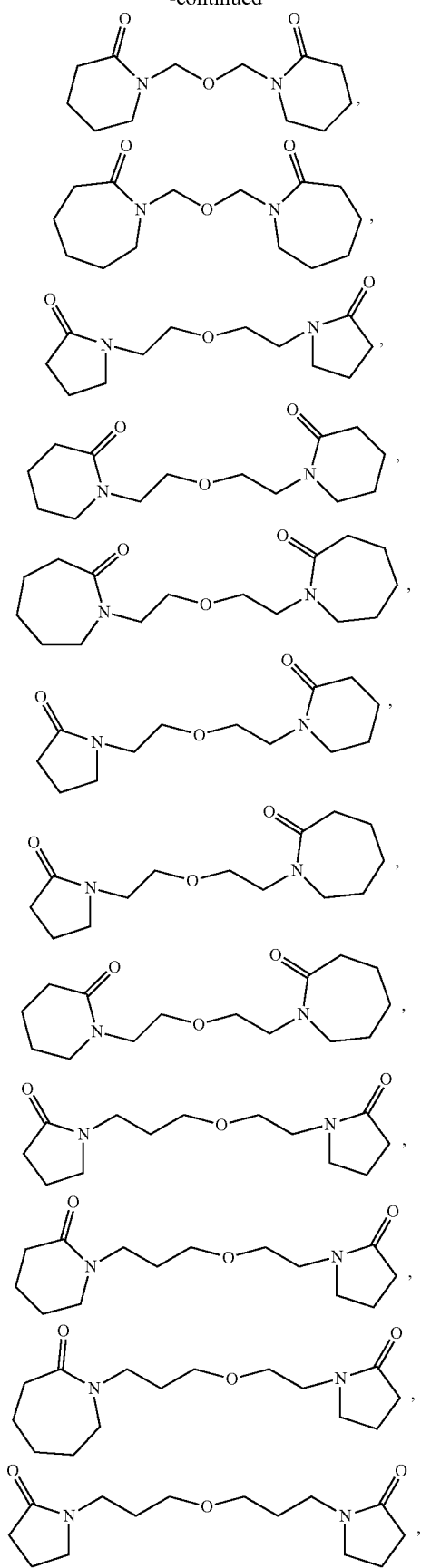

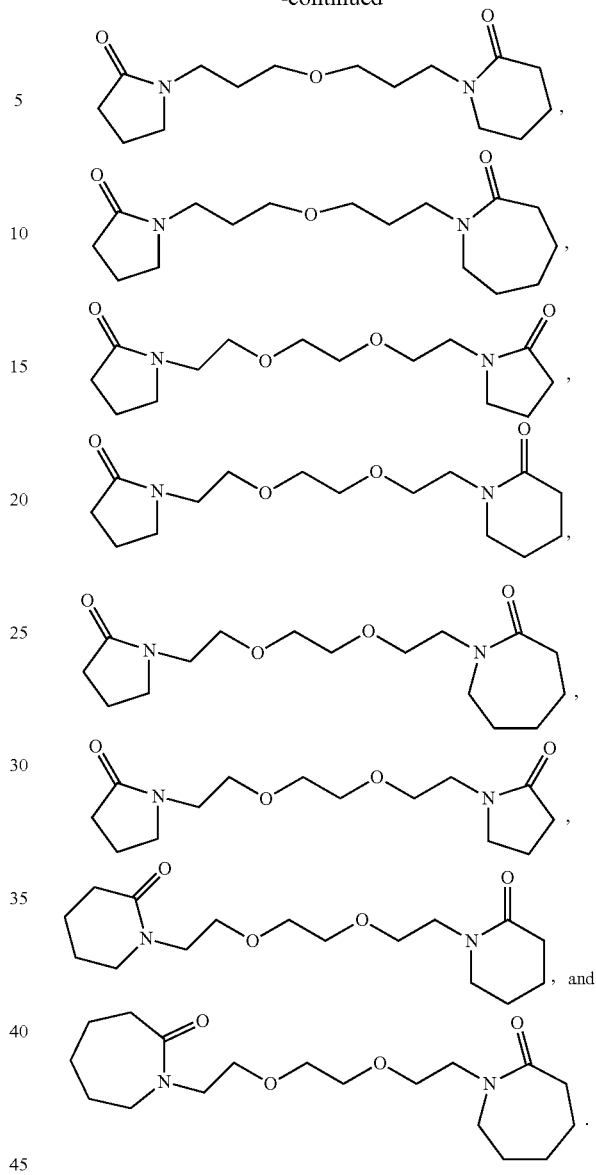

Further non-limiting examples of compounds comprising at least one ether, thioether, and/or imine moiety and at least two lactam moieties may be found in U.S. Pat. No. 9,993, 559 the disclosure of which is herein incorporated in its entirety by reference.

In one non-limiting embodiment, the halogen that is a component of the complexes according to the disclosed and/or claimed inventive concept(s) is selected from the group consisting of molecular iodine, molecular bromine, iodides, bromides, and combinations thereof.

In a second aspect, the disclosed and/or claimed inventive concept(s) provides a composition comprising a complex of at least one halogen and a compound comprising at least one ether, thioether, and/or imine moiety and at least two lactam moieties.

In one non-limiting embodiment, the compound comprising at least one ether, thioether, and/or imine moiety and at least two lactam moieties that is a component of the compositions according to the disclosed and/or claimed inventive concept(s) has a structure:

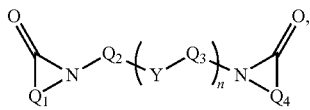

wherein each Y is independently selected from the group consisting of —O—, —S—, —NR—, and combinations thereof; each R is independently selected from the group consisting of hydrogen, alkyl,

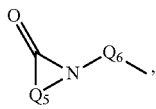

and combinations thereof; each $Q_1$, $Q_2$, $Q_3$, $Q_4$, $Q_5$ and $Q_6$ is independently a functionalized or unfunctionalized alkylene; and n has a value≥1.

In one non-limiting embodiment, the composition is a personal care composition, home care composition, pharmaceutical composition, antimicrobial composition, preservative composition, disinfectant composition, biocidal composition, germicidal composition, coating composition, construction composition, nutritional composition, agricultural composition, adhesive composition, oilfield composition, household, industrial and institutional composition, cementing fluid, servicing fluid, gravel packing mud, fracturing fluid, completion fluid, work-over fluid, spacer fluid, drilling mud, ink, paper, polish, membrane, metal working fluid, plastic, textile, printing composition, lubricant, detergent, battery composition, or glass coating composition.

In one non-limiting embodiment, the composition is a personal care composition, home care composition, pharmaceutical composition, antimicrobial composition, preservative composition, disinfectant composition, biocidal composition, germicidal composition, or coating composition.

In a third aspect, the disclosed and/or claimed inventive concept(s) provides a personal care, home care, pharmaceutical, antimicrobial, disinfectant, biocidal, germicidal, or coating composition comprising a complex of at least one halogen and a compound comprising at least one ether, thioether, and/or imine moiety and at least two lactam moieties.

In one embodiment, the halogen is selected from the group consisting of molecular iodine, molecular bromine, iodides, bromides, and combinations thereof.

In one non-limiting embodiment, the compound comprising at least one ether, thioether, and/or imine moiety and at least two lactam moieties that is a component of the personal care, home care, pharmaceutical, antimicrobial, disinfectant, biocidal, germicidal, or coating composition according to the disclosed and/or claimed inventive concept(s) has a structure:

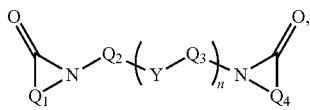

wherein each Y is independently selected from the group consisting of —O—, —S—, —NR—, and combinations thereof; each R is independently selected from the group consisting of hydrogen, alkyl,

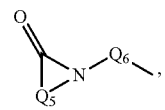

and combinations thereof; each $Q_1$, $Q_2$, $Q_3$, $Q_4$, $Q_5$ and $Q_6$ is independently a functionalized or unfunctionalized alkylene; and n has a value≥1.

In one non-limiting embodiment, the compositions according to the disclosed and/or claimed inventive concept(s) may further comprise at least one additive selected from the group consisting of UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

In one non-limiting embodiment, the personal care, home care, pharmaceutical, antimicrobial, disinfectant, biocidal, germicidal, or coating composition according to the disclosed and/or claimed inventive concept(s) may further comprise at least one additive selected from the group consisting of UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

Any range of composition pH may be used. In aspects wherein the composition may be applied to keratinous material, the pH may range from about 2 to 12. The pH may be adjusted to a desired value by means of adding one or more acidifying or alkalinizing agents that are well-known in the state of the art. For example, the composition can contain at least one alkalizing or acidifying agent in amounts from about 0.01% to about 30% based on the total weight of the composition.

Non-limiting examples of acidifying or acidic pH adjusting agents include organic acids, such as citric acid, acetic acid, carboxylic acids, α-hydroxyacids, β-hydroxyacids, α,β-hydroxyacids, salicylic acid, tartaric acid, lactic acid, glycolic acid, natural fruit acids, and combinations thereof. In addition, inorganic acids, for example hydrochloric acid, nitric acid, sulfuric acid, sulfamic acid, phosphoric acid, and combinations thereof can be utilized.

Non-limiting examples of alkalizing or alkaline pH adjusting agents include ammonia, alkali metal hydroxides (such as sodium hydroxide and potassium hydroxide), ammonium hydroxide, alkanolamines (such as mono-, di- and triethanolamine), diisopropylamine, dodecylamine, diisopropanolamine, aminomethyl propanol, cocamine, oleamine, morpholine, triamylamine, triethylamine, tromethamine (2-amino-2-hydroxymethyl)-1,3-propanediol), and tetrakis(hydroxypropyl)ethylenediamine, hydroxyalkylamines and ethoxylated and/or propoxylated ethylenediamines, alkali metal salts of inorganic acids, such as sodium borate (borax), sodium phosphate, sodium pyrophosphate, and the like, and mixtures thereof.

Non-limiting examples of alkalizing agent can be chosen from ammonia, alkali carbonates, alkanolamines, like mono-, di- and triethanolamines, as well as their derivatives, sodium or potassium hydroxides and compounds of the following formula:

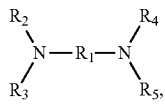

wherein $R_1$ may be a propylene residue that may be optionally substituted with an hydroxyl group or a $C_1$-$C_4$ alkyl radical; $R_2$, $R_3$, $R_4$ and $R_5$ are identical or different and represent a hydrogen atom, a $C_1$-$C_4$ alkyl radical or $C_1$-$C_4$ hydroxyalkyl radical.

The compositions according to the disclosed and/or claimed inventive concept(s) may be presented in different product forms, non-limiting examples of which include: solids, semi-solids, solutions, oils, lotions, pastes, creams, ointments, liquids, sprays, gels, W/O emulsions, O/W emulsions, milks, suspensions, microemulsions, dispersions, and microencapsulated products.

In one non-limiting embodiment, the compositions according to the disclosed and/or claimed inventive concept(s) may be used in treating skin conditions, non-limiting examples of which include dermatitis, wounds, infections, burns, rashes, and herpes. These compositions may be staining, substantially non-staining, or essentially non-staining.

The amount of each additive in the compositions according to the disclosed and/or claimed inventive concept(s) may vary depending on the type of composition, the function and/or physicochemical property of the ingredient, and the amount of other co-ingredients. The precise amount of each ingredient may be easily determined by any person skilled in the related arts.

In one non-limiting embodiment, the compositions according to the disclosed and/or claimed inventive concept(s) may optionally comprise secondary antimicrobial agent(s).

Non-limiting examples of suitable water insoluble, non-cationic antimicrobial agents include: halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, halogenated carbanilides, and blends thereof.

Non-limiting examples of suitable water soluble antimicrobial agents include: quaternary ammonium salts, bis-biguanide salts, triclosan monophosphate, and blends thereof.

The quaternary ammonium agents include those in which one or two of the substituents on the quaternary nitrogen has a carbon chain length (typically alkyl group) from about 8 to about 20, typically from about 10 to about 18 carbon atoms, while the remaining substituents (typically alkyl or benzyl group) have a lower number of carbon atoms, such as from about 1 to about 7 carbon atoms, typically methyl or ethyl groups.

Non-limiting examples of suitable quaternary ammonium antibacterial agents include: Dodecyl trimethyl ammonium bromide, tetradecylpyridinium chloride, domiphen bromide, n-tetradecyl-4-ethyl pyridinium chloride, dodecyl dimethyl (2-phenoxyethyl)ammonium bromide, benzyl dimethyl-stearyl ammonium chloride, cetyl pyridinium chloride, quaternized 5-amino-1,3-bis(2-ethyl-hexyl)-5-methyl hexahydropyrimidine, benzalkonium chloride, benzethonium chloride, methyl benzethonium chloride, and blends thereof.

Other antimicrobial compounds are bis[4-(R-amino)-1-pyridinium]alkanes as disclosed in U.S. Pat. No. 4,206,215. Other antimicrobials such as copper salts, zinc salts and/or stannous salts may also be included. Also useful are enzymes, including endoglycosidase, papain, dextranase, mutanase, and blends thereof. Such antimicrobial agents are disclosed in U.S. Pat. Nos. 2,946,725 and 4,051,234. The antimicrobial agents may also comprise chlorhexidine, triclosan, and flavor oils such as thymol. Triclosan and other agents are disclosed in U.S. Pat. Nos. 5,015,466 and 4,894,220.

In non-limiting aspects, one or more preservatives may be included.

Non-limiting examples of suitable preservatives include: benzoic acid, sorbic acid, dehydroacetic acid, diazolidinyl ureas, imidazolidinyl ureas, salicylic acid, piroctone olamine, DMDM hydantoin, IPBC (iodopropynyl butylcarbamate), triclosan, bronopol, formaldehyde, isothiazolinones, nitrates/nitrites, parabens, phenoxyethanol, potassium sorbate, sodium benzoate, sulphites, sulphur dioxide, and blends thereof.

In non-limiting aspects, preservative boosters/solvents may be incorporated, non-limiting examples of which include: caprylyl glycol, hexylene glycol, pentylene glycol, ethylhexylglycerin, caprylhydroxamic acid, caprylohydroxamic acid, glyceryl caprylate, and blends thereof.

Non-limiting examples of suitable liquid carriers include: water, alcohols, oils, esters, and blends thereof.

The compositions of the invention may also be in the form of aqueous or hydro-alcoholic solutions.

The physiological and cosmetically acceptable medium may consist exclusively of water, a cosmetically acceptable solvent, or a blend of water and a cosmetically acceptable solvent, such as a lower alcohol composed of C1 to C4, such as ethanol, isopropanol, t-butanol, n-butanol, alkylene glycols such as propylene glycol, and glycol ethers.

In one non-limiting embodiment, the compositions according to the disclosed and/or claimed inventive concept(s) may optionally comprise one or more surfactants. Surfactants serve in solubilizing, dispersing, emulsifying and/or reducing the interfacial tension. Surfactants may be chosen from anionic, nonionic, amphoteric, zwitterionic, or cationic surfactants, or blends thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are non-limiting examples of anionic surfactants of this type.

Non-limiting examples of suitable anionic surfactants include: sarcosinates, taurates, isethionates, sodium lauryl sulfoacetate, sodium laureth carboxylate, and sodium dodecyl benzenesulfonate. Also suitable are alkali metal or ammonium salts of surfactants such as the sodium and potassium salts of the following: lauroyl sarcosinate, myristoyl sarcosinate, palmitoyl sarcosinate, stearoyl sarcosinate, and oleoyl sarcosinate.

Non-limiting examples of suitable cationic surfactants include: derivatives of aliphatic quaternary ammonium compounds having at least one long alkyl chain containing from about 8 to about 18 carbon atoms, such as, lauryl trimethylammonium chloride, cetyl pyridinium chloride, cetyl trimethylammonium bromide, di-isobutylphenoxyethyl-dimethylbenzylammonium chloride, coconut alkyltrimethylammonium nitrite, cetyl pyridinium fluoride, and blends thereof. Further suitable are quaternary ammonium fluorides having detergent properties such as compounds described in U.S. Pat. No. 3,535,421. Certain cationic surfactants may act as germicides in the compositions disclosed herein.

Nonionic surfactants useful herein include compounds produced by the condensation of alkylene oxide groups (hydrophilic in nature) with an organic hydrophobic compound which may be aliphatic or alkylaromatic in nature.

Non-limiting examples of suitable nonionic surfactants include: poloxamers (sold under the trade name Pluronic® by BASF Corporation), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and blends thereof.

Non-limiting examples of suitable zwitterionic surfactants include betaines and derivatives of aliphatic quaternary ammonium compounds in which the aliphatic radicals can be straight chain or branched, and which contain an anionic water-solubilizing group, e.g., carboxy, sulfonate, sulfate, phosphate, or phosphonate.

Non-limiting examples of suitable betaines include: decyl betaine or 2-(N-decyl-N,N-dimethylammonio)acetate, coco betaine or 2-(N-coc-N,N-dimethyl ammonio)acetate, myristyl betaine, palmityl betaine, lauryl betaine, cetyl betaine, stearyl betaine, and blends thereof. The amidobetaines are exemplified by cocoamidoethyl betaine, cocoamidopropyl betaine, lauramidopropyl betaine, and the like. The betaines of choice include cocoamidopropyl betaines such as lauramidopropyl betaine. Suitable betaine surfactants are disclosed in U.S. Pat. No. 5,180,577.

Other surfactants such as fluorinated surfactants may also be incorporated within the compositions of the invention.

Also suitable as surfactants are the following commercial products:

(1) Alkanolamides, under the trade names Amidex™ and Schercomid™; amido-amines, under the trade names Katemul™ and Schercodine™; amine oxides, under the trade names Chemoxide™ and Schercamox™; amphoterics, under the trade names Chembetaine™, Schercotaine™ and Schercoteric™; imidazolines, under the trade name Schercozoline™; pearlizing agents, under the trade name Quickpearl™; performance concentrates, under the trade names Sulfochem™ and Chemoryl™; soaps (potassium cocoate and potassium soyate); specialty ethoxylates, under the trade name Chemonic™; specialty quats under the trade names Quatrex™ and Schercoquat™; sulfates, under the trade name Sulfochem™; and sulfosuccinates, under the trade name Chemccinate™ from Lubrizol.

(2) Avaniel, Cremaphore®, Jordapan®, and Pluracare® from BASF Corp.

(3) Miracare® SLB, Mackam® Bab, Mackanate® Ultra SI, Miranol® Ultra, and Miracare® Plaisant from Rhodia.

(4) Stepan® Pearl 2, Stepan® Pearl 4, Stepan® Pearl Series, Neobee® M-20, Stepan® PTC, Amphosol® 2CSF, Steol®, Stepan-Mild® GCC, Stepan® SLL-FB, Stepanol® AM, Stepan® PB, Alpha-Step® BSS-45, Bio-Terge® 804, Stepan-Mild® L3, Stepan® SLL-FB, Stepan® SSL-CG, and Stepanol® CFAS-70 from Stepan Company.

Also suitable as surfactants are those described in the book *Surfactants in Personal Care Products and Decorative Cosmetics*, Third Edition, 2006, CRC Press. The disclosure is herein incorporated in its entirety by reference.

In one non-limiting embodiment, the compositions according to the disclosed and/or claimed inventive concept(s) may further comprise one or more thickener(s) and/or viscosifier(s).

Non-limiting examples of suitable thickeners and/or viscosifiers include: Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/ C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; alcaligenes polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *Arachis hypogaea* (peanut) flour; ascorbyl methylsilanol pectinate; *astragalus* gummifer gum; attapulgite; *Avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *caesalpinia spinosa* gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; citrus aurantium *dulcis* (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/ oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/isophthalates/SIP copolymer; dihydroabietyl behenate; dihydrogenated tallow benzylmonium hectorite; dihydroxyaluminum aminoacetate; dimethicone/PEG- 10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; *glycine soja* (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylenediamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; macrocystis pyrifera (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/™ MG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/™ MG copolymer; PEG-150 pentaerythrityl tetrastearate; PEG-4 rapeseedamide; PEG-150/stearyl alcohol/SMDI copolymer; *phaseolus angularis* seed powder; polianthes *tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; *sclerotium* gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *Solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; sterculia *urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *Triticum vulgare* (wheat) germ powder; *Triticum vulgare* (wheat) kernel flour; *Triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides; *Zea mays* (corn) starch; and blends thereof.

Also suitable as thickeners and/or viscosifiers are the following commercial products:

(1) Aqualon™ carboxymethylcellulose, Benecel™ methylcellulose and hydroxypropyl methylcellulose, Blanose™ sodium carboxymethylcellulose, Klucel™ hydroxypropylcellulose, Natrosol™ hydroxyethylcellulose, Natrosol™ Plus and PolySurf™ cetyl modified hydroxyethylcellulose, n-Hance™ cationic guar, n-Hance™ HP Series hydroxypropyl guar, n-Hance™ SP-100 conditioning polymer, and Supercol™ guar gum from Ashland Specialty Ingredients.

(2) Carbopol® Polymers, Fixate™ PLUS Polymer, Glucamate™ Thickeners, Amidex™ Surfactants, Chembetaine™ Surfactants, Chemoxide™ Surfactants, Chemonic™ Surfactants, Chemccinate™ Surfactants, Amidex™ BC-24 Surfactant, Chemoryl™ LB-30 Surfactant, Novethix™ L-10 Polymer, Ceralan™ Lanolin Product, Pemulen™ TR-1 Polymeric Emulsifier, Pemulen™ TR-2 Polymeric Emulsifier, Hydramol™ PGPD Ester, Schercodine™ M Amido-Amine, Schercodine™ P Amido-Amine, Schercomid™ Diethanolamides from The Lubrizol Corporation.

(3) Salcare® and Luvigel® from BASF Corporation.

(4) Aculyn™ 22, Aculyn™ 28, Aculyn™ 33, Aculyn™ 38, and Aculyn™ 44 from The Dow Chemical Company.

(5) Ammonyx® C and Stepan-Mild® GCC from Stepan Company.

(6) Stabileze™, Rapithix™ A-60, Rapithix™ A-100, Ultrathix™ P-100, Lubrajel™ and FlexiThix™ from Ashland Specialty Ingredients.

Also suitable as a thickener/rheology modifier are lightly- to moderately-crosslinked polyvinylpyrrolidones. Disclosures of these polymers are provided in the following publications, each of which is herein incorporated in its entirety by reference: U.S. Pat. Nos. 5,073,614; 5,312,619; 5,139,770; 5,716,634; 5,470,884; 5,759,524; 5,997,887; 6,024,942; as well as international application PCT/US10/26973, PCT/US10/26976, PCT/US10/26940, PCT/US11/32993, and PCT/US11/34515.

In one non-limiting embodiment, the compositions according to the disclosed and/or claimed inventive concept(s) may further comprise natural extracts and/or natural products. Extensive details on natural products that can be used in personal care compositions is provided in book chapter "Chemistry of Cosmetics, Comprehensive Natural Products II" in *Chemistry and Biology*; volume 3, 2010.

Methods of Synthesis

The compounds according to the disclosed and/or claimed inventive concept(s) may be prepared according to the examples set out below. These examples are presented herein for purposes of illustration of the disclosed and/or claimed inventive concept(s) and are not intended to be limiting, for example, the preparations of the compounds.

EXAMPLE

Example 1: Synthesis of Hydrogen Triiodide Complex of Bis-Pyrrolidone Ether (Compound 1)

Compound 1

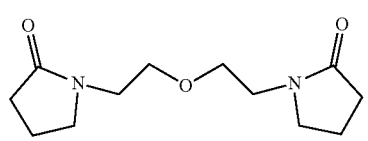

Compound 1 (0.099 g, 0.41 mmol) was dissolved in dichloromethane (3 mL) and a dichloromethane solution of molecular iodine (2 mL, 0.106 g, 0.42 mmol) was added producing a color change from purple to brown. Aqueous hydroiodic acid (56.5%, 0.097 g, 0.43 mmol) was added and the mixture allowed to stand for 5 minutes. To the resulting stirred mixture was added excess n-hexane (50 mL) resulting in the formation of a brown oil. Prolonged stirring with a magnetic follower and periodic ultrasonication resulted in the formation of a brown precipitate which was isolated by filtration, washed with n-hexane and air dried. The yield was 0.077 g (0.12 mmol) at 30%. A sample for X-ray diffraction was recrystallized by slow diffusion of diethyl ether vapor into a dichloromethane solution of the target compound resulting in orange-brown plates.

Crystal data for $HI_3$ complex of Compound 1: $C_{12}H_{21}N_2O_3I_3$, M=622.01, monoclinic, space group $P2_1/n$, a=9.8888(7), b=11.1703(8), c=17.4138(12) Å, β=105.943(2)°, U=1849.6(2) Å$^3$, F(000)=1160, Z=4, $D_c$=2.234 mg m$^{-3}$, μ=5.078 mm$^{-1}$, T=120.0(1)K. 39644 reflections were collected, yielding 5635 unique data ($R_{merg}$=0.0603). Final $wR_2(F^2)$=0.0812 for all data (185 refined parameters), conventional $R_1$ (F)=0.0325 for 4676 reflections with I≥2σ, GOF=1.059.

What is claimed is:

1. A complex of at least one halogen selected from the group consisting of molecular iodine, molecular bromine, iodides, bromides, and combinations thereof and a compound having a structure selected from the group consisting of:

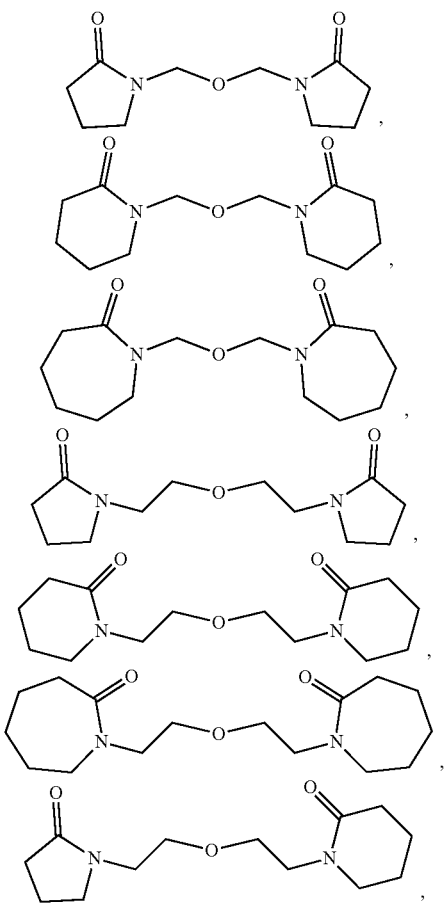

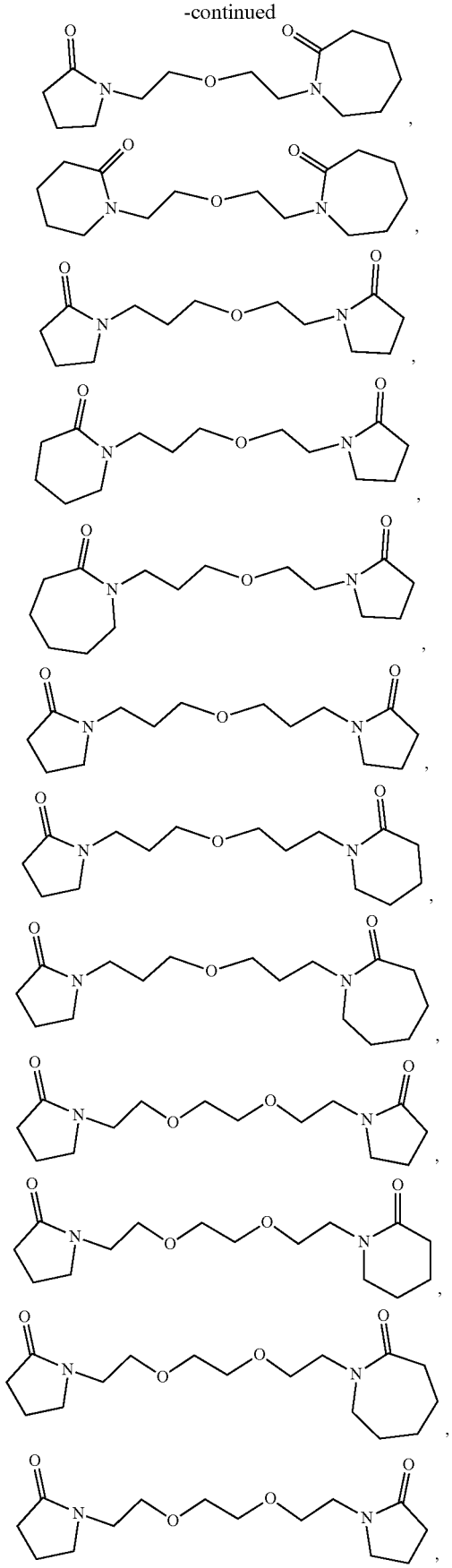
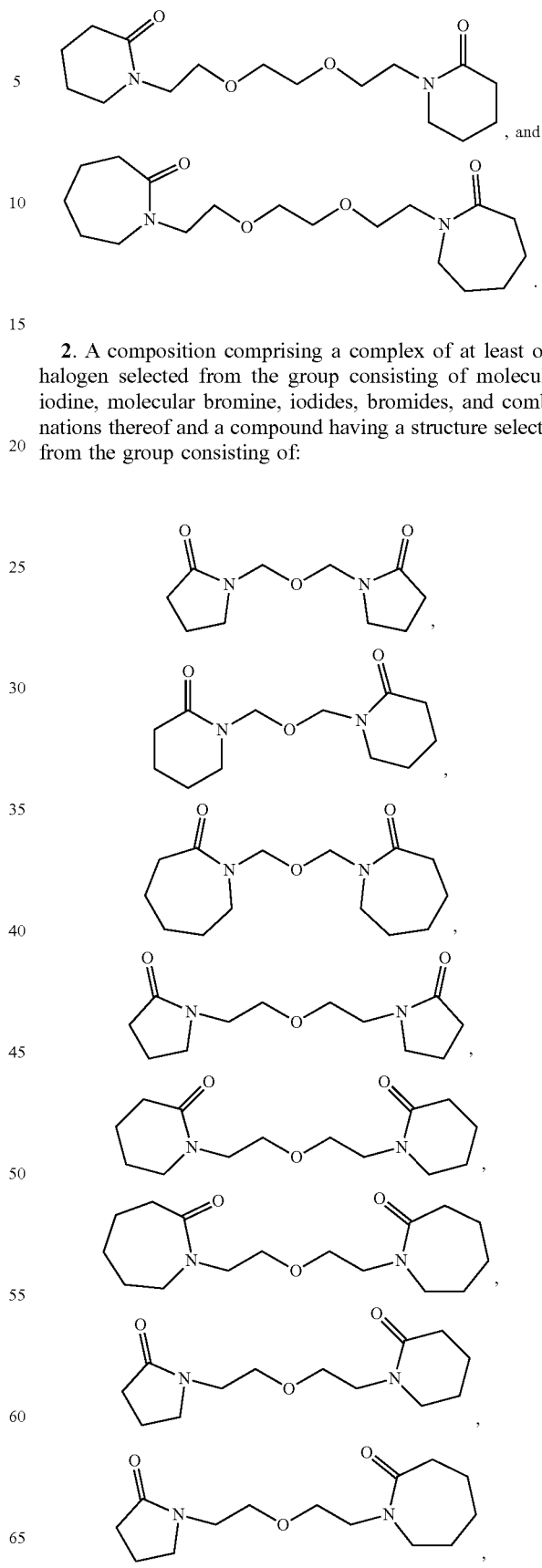
2. A composition comprising a complex of at least one halogen selected from the group consisting of molecular iodine, molecular bromine, iodides, bromides, and combinations thereof and a compound having a structure selected from the group consisting of:

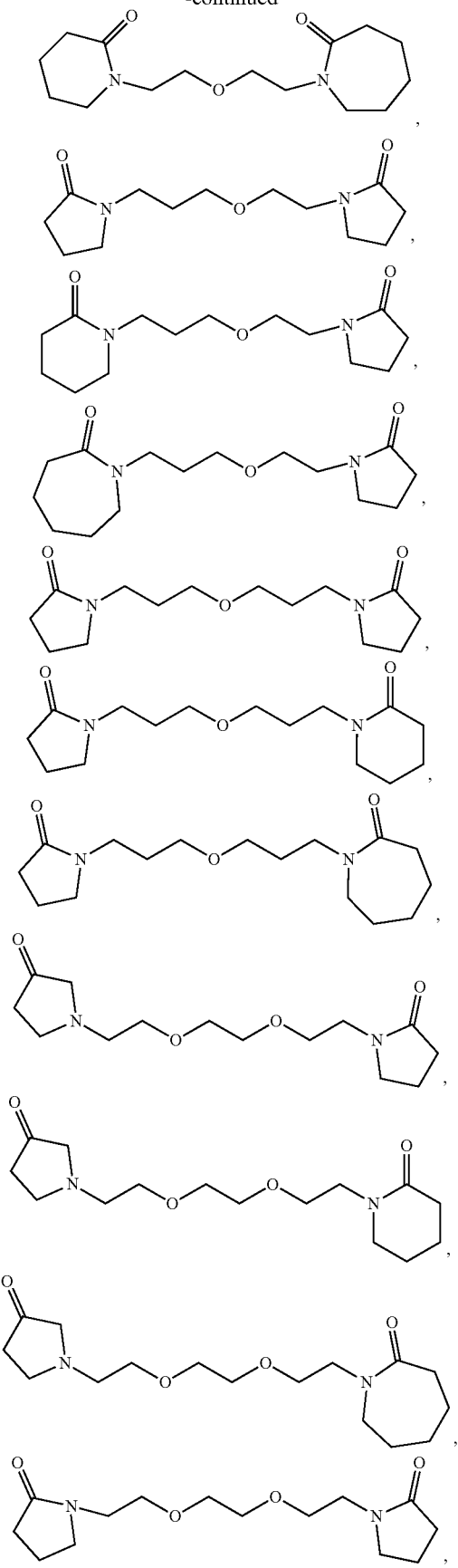

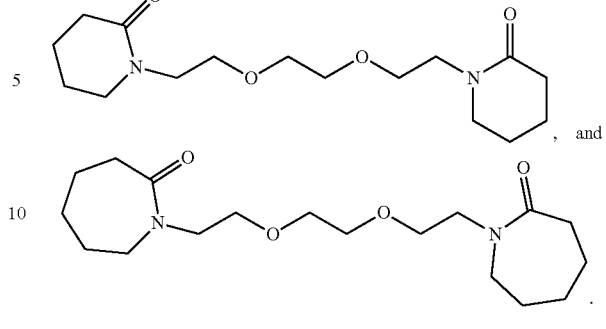

3. The composition according to claim 2 that is a personal care composition, home care composition, pharmaceutical composition, antimicrobial composition, preservative composition, disinfectant composition, biocidal composition, germicidal composition, coating composition, construction composition, nutritional composition, agricultural composition, adhesive composition, oilfield composition, household, industrial and institutional composition, cementing fluid, servicing fluid, gravel packing mud, fracturing fluid, completion fluid, work-over fluid, spacer fluid, drilling mud, ink, paper, polish, membrane, metal working fluid, plastic, textile, printing composition, lubricant, detergent, battery composition, or glass coating composition.

4. The composition according to claim 3 that is a personal care composition, home care composition, pharmaceutical composition, antimicrobial composition, disinfectant composition, biocidal composition, germicidal composition, or coating composition.

5. The composition according to claim 3 further comprising at least one additive selected from the group consisting of UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

6. A personal care, home care, pharmaceutical, antimicrobial, disinfectant, biocidal, germicidal, or coating composition comprising a complex of at least one halogen selected from the group consisting of molecular iodine, molecular bromine, iodides, bromides, and combinations thereof and a compound having a structure selected from the group consisting of:

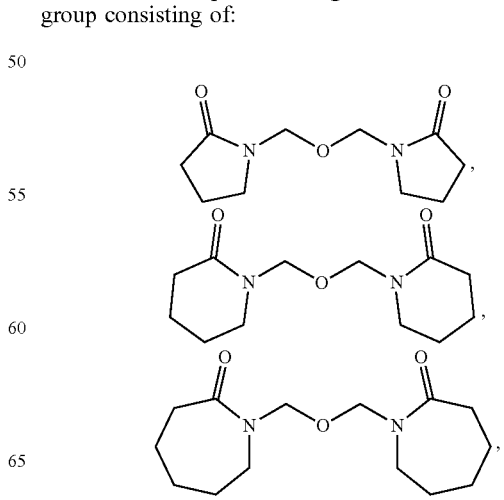

-continued

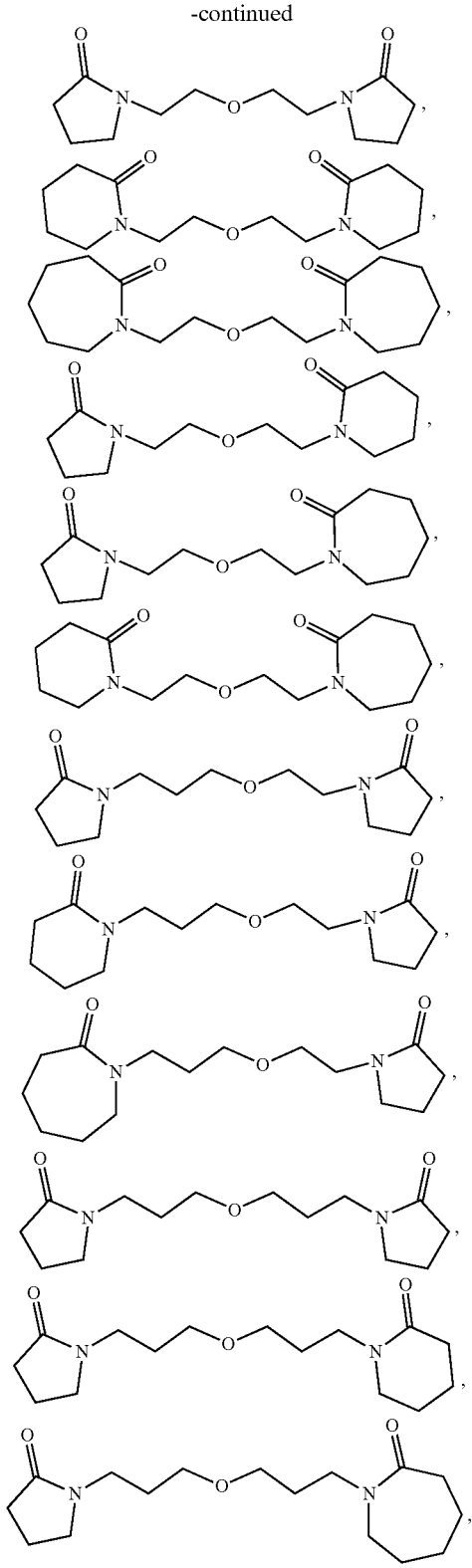

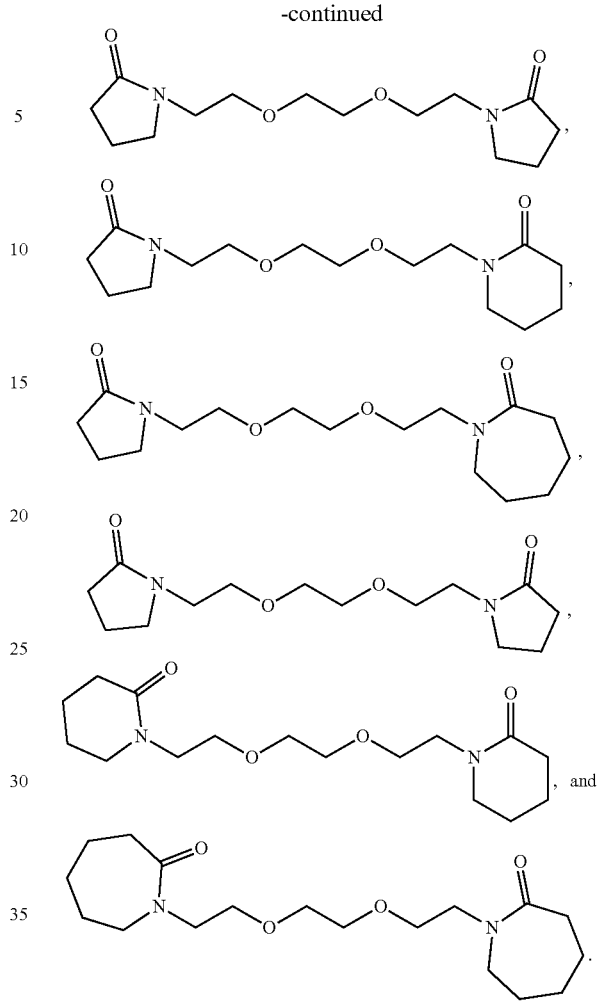

, and

7. The personal care, home care, pharmaceutical, antimicrobial, disinfectant, biocidal, germicidal, or coating composition according to claim 6 wherein said halogen is selected from the group consisting of molecular iodine, molecular bromine, iodides, bromides, and combinations thereof.

8. The personal care, home care, pharmaceutical, antimicrobial, disinfectant, biocidal, germicidal, or coating composition according to claim 6 further comprising at least one additive selected from the group consisting of UV actives, UV active solubilizers, oils, waxes, solvents, emulsifiers, preservatives, antioxidants, antiradical protecting agents, vitamins, perfumes, insect repellants, dyes, pigments, humectants, fillers, thickeners, film formers, stabilizers, buffers, spreading agents, pearlizing agents, electrolytes, acids, bases, crystalline structuring agents, abrasives, pharmaceutically or cosmetically acceptable excipients, and combinations thereof.

* * * * *